United States Patent [19]

Minten et al.

[11] Patent Number: 4,677,078

[45] Date of Patent: * Jun. 30, 1987

[54] OXYGEN MONITORING DEVICE AND METHOD

[75] Inventors: Karl Minten, La Hoya, Calif.; William Krug, Hoffman Estates, Ill.

[73] Assignee: Gould Inc., Rolling Meadows, Ill.

[*] Notice: The portion of the term of this patent subsequent to Oct. 1, 2002 has been disclaimed.

[21] Appl. No.: 607,512

[22] Filed: May 7, 1984

[51] Int. Cl.$^4$ .................................................. G01N 21/78
[52] U.S. Cl. ..................................... 436/136; 422/87; 422/91; 436/164; 436/904
[58] Field of Search ............... 436/151, 136, 164, 167, 436/904; 422/69, 56, 57, 88, 86, 87, 90, 91; 260/429 R; 73/23, DIG. 4

[56] References Cited

U.S. PATENT DOCUMENTS

| | | | |
|---|---|---|---|
| 2,232,622 | 2/1941 | Moses et al. | 23/255 |
| 2,741,544 | 4/1956 | Chaikin et al. | 23/255 |
| 2,800,397 | 7/1957 | Offutt et al. | 23/232 |
| 2,895,807 | 7/1959 | Sorg et al. | 23/255 |
| 3,114,610 | 12/1963 | Gafford et al. | 23/255 |
| 3,164,004 | 1/1965 | King, Jr. | 73/23 |
| 3,194,053 | 7/1965 | Shang | 73/23 |
| 3,260,104 | 7/1966 | King, Jr. | 73/23 |
| 3,343,044 | 9/1967 | King, Jr. et al. | 317/146 |
| 3,538,133 | 11/1970 | Knoth, Jr. | 260/429 |
| 3,694,164 | 9/1972 | Guenther | 422/88 X |
| 3,744,296 | 7/1973 | Beltzer | 73/23 |
| 3,754,867 | 8/1973 | Guenther | 422/91 |
| 3,870,469 | 3/1975 | Walker | 23/232 E |
| 3,920,402 | 11/1975 | Afanasiev et al. | 422/91 |
| 4,027,084 | 5/1977 | Tkatchenko | 526/27 |
| 4,032,297 | 6/1977 | Lyshkow | 23/254 E |
| 4,032,617 | 6/1977 | Gay | 423/219 |
| 4,042,333 | 8/1977 | Dell et al. | 23/232 R |
| 4,081,769 | 3/1978 | Shreve | 333/72 |
| 4,096,740 | 6/1978 | Sallee . | |
| 4,100,811 | 7/1978 | Callen et al. | 73/654 |
| 4,111,036 | 9/1978 | Frechette et al. | 73/23 |
| 4,230,828 | 10/1980 | Gaul, Jr. et al. | 525/153 |
| 4,245,997 | 1/1981 | Wiesner | 422/91 X |
| 4,251,452 | 2/1981 | McAuliffe et al. | 260/429 R |
| 4,306,877 | 12/1981 | Lubbers | 422/91 X |
| 4,312,228 | 1/1982 | Wohltjen | 73/597 |
| 4,313,338 | 2/1982 | Abe et al. | 73/23 |
| 4,323,543 | 4/1982 | McAuliffe et al. | 423/219 |
| 4,343,715 | 8/1982 | Bonaventura et al. | 252/186 |
| 4,361,026 | 11/1982 | Muller et al. | 73/23 |
| 4,442,297 | 4/1984 | Hill et al. | 260/429 R X |

OTHER PUBLICATIONS

Hosseiny et al., *Inorganica Chimica Acta*, 39 (1980) 227-231.
Clark, Jr., *Trans. Amer. Soc. Artif. Intern. Organs*, vol. 2, pp. 41-48 (1956).
Bahmet et al, *Anal. Chem.*, vol. 43, pp. 803-805 (1971).
Hersch, *Amer. Lab.*, (Aug. 1983), pp. 29-36.
Janata et al., "Ion Selective Electrodes", in Freiser (ed), *Analytical Chemistry*, vol. 2, pp. 124-126 (1980).
Garverick et al., *IEEE Trans. Electron Dev.*, vol. 29, pp. 90-94 (1982).
Mins, III-Engineer's Notebook II, p. 87 (1982).
Hlavey et al., *Anal. Chem.*, vol. 49, No. 13, pp. 1890-1898 (1977).
McAuliffe et al, "Working Haem Analogues; Reversible Oxygenation of the Manganese-Tertiary Phosphine Complexes MnLX$_2$", JCS Chemical Communications 1979, pp. 736-738 (1979).

*Primary Examiner*—Arnold Turk
*Attorney, Agent, or Firm*—J. M. Walder; E. E. Sachs; G. P. Edgell

[57] ABSTRACT

The present invention relates to a novel method and apparatus which can provide continuous monitoring of the oxygen content of a gas over an indefinite period of time and at a minimal cost.

In the novel apparatus of the present invention, a light source and a light sensitive detector are disposed within the atmosphere to be measured, and a polymeric film formed from a manganese tertiary phosphine polymer complex is deposited between the light source and the detector. As oxygen pressure increases or decreases a change in color intensity of the film takes place which controls passage of light from the light source to the detector. The detector in turn is suitably connected to an audio and/or visual warning device and/or a recorder which will provide the desired form of warning.

25 Claims, 2 Drawing Figures

U.S. Patent
Jun. 30, 1987
4,677,078
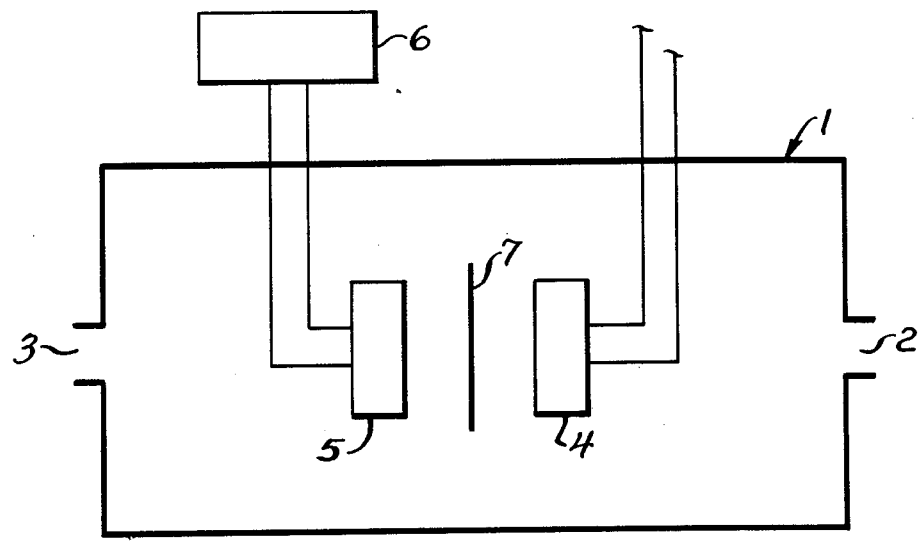
FIG. 1
FIG. 2
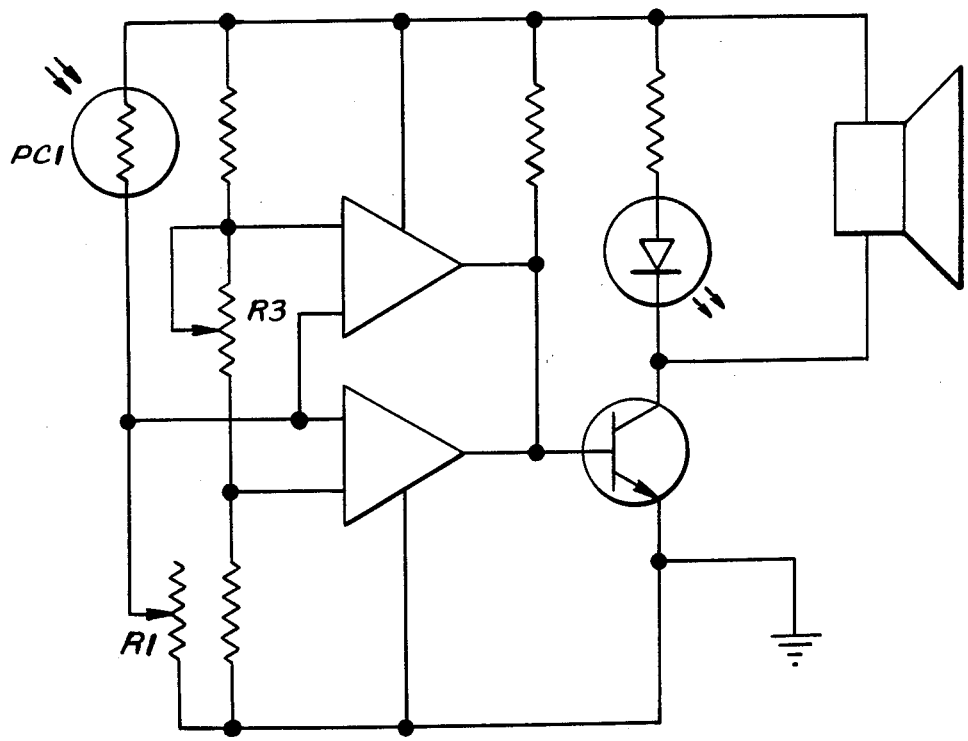

OXYGEN MONITORING DEVICE AND METHOD

BACKGROUND OF THE INVENTION

The present invention relates to a novel method and apparatus for monitoring the level of oxygen in a feed stream or within the atmosphere of a defined space such as an oxygen chamber, oxygen tent, a room, or the like.

In the past there have been a number of procedures and apparatus proposed for the monitoring or analysis or sampling of gases. These include electrochemical methods, mass spectrometry methods, CHEMFET devices, charger flow transistors, gas chromatographic and other colorimetric procedures. In general, these involved extremely expensive and sophisticated equipment and techniques or mechanisms which were not truly reversible and/or indefinitely continuous. In most cases, they relied on a chemical reaction by the gas which would provide a corresponding change in pH thereby triggering a color change in an indicator as a colorimetric chemical reaction which was not quickly and fully reversible. Also, such systems were obviously subject to the vagaries of other gases which might be present particularly the relative amount of humidity present.

The earliest systems for monitoring of gases generally related to gases such as carbon dioxide, hydrogen sulfide, halogens and the like. These systems were colorimetric in nature, but the colorimetric reaction was not immediately and completely self reversing in response to a reversal of the change in concentration of the gas being monitored.

As examples of one type of system taught by the prior art, mention might be made of U.S. Pat. No. 3,754,867 Karl R. Guenther, in which the carbon dioxide content of ambient air is monitored using a thin layer of chemical which will absorb carbon dioxide forming an acid which will provide a change in pH. An indicator present in the film changes color. The system circumvents problems of humidity by using an ionizing solvent having a vapor pressure in the range of 0–10 mm at temperatures up to 150° F., and compatible with the other components of the system.

Another method is proposed by U.S. Pat. No. 3,114,610 to Gafford et al., using very sophisicated analyzing equipment to measure the particular presence of a constituent of a gas, which constituent produces acidic or basic solutions. Again, basically a one-way system in which the sample must be either neutralized, or the indicator replaced, or the instrument recalibrated before further sampling can continue.

U.S. Pat. No. 2,232,622 to Moses et al., and U.S. Pat. No. 2,741,544 to Chaikin et al., provide an alternate method in which continuous sampling is possible over a finite period of time. Moses et al., relates to the monitoring of hydrogen sulfide, and Chaikin et al., relates to the apparatus of fluoride analysis. They are, however, very similar methods, in that continuous analysis over a finite period of time is achieved by winding forward a continuous strip of tape impregnated with the indicator. As with Guenther and Gafford, however, the system relies on a change in pH to trigger a color change in an indicator.

All of the foregoing systems have certain basic limitations. They can only measure gases which provide an acidic or basic solution such as carbon dioxide, hydrogen sulfide, halogen, or the like; and they are operable, at best, intermittently or over a relatively finite period of time. In addition, those which do provide for some measure of continuous monitoring, such as Moses et al., involve very cumbersome and relatively expensive apparatus, such as a drive motor and the like.

The range of oxygen detection methods is large but generally very sophisticated and more expensive than those described above and includes such diverse means as electrochemical reactions and cells, optical fiber monitors based on fluorescence quenching of dyes or colorimetric oxygen reactions, CHEMFETS and charge-flow transistor devices, anaerobic bacterial activity, mass spectrometry, gas chromatography and the addition of odorants of other detectable trace gas additives to the oxygen supply. However, use of most such techniques is far from commercialization, while others are suitable only for certain limited applications. None of these techniques provide an inexpensive continuous simple procedure for in-line monitoring of oxygen level in a fuel stream or enclosed area.

The Clark cell [L. C. Clark, Jr., Trans. Amer. Soc. Artif. Intern. Organs, 2, 41–48 (1965)] is the most commonly used electrometric oxygen sensor available today. It is based on polarographic principles by which, for a given applied voltage, the current between two electrodes is directly proportional to the oxygen partial pressure in the environment.

A very similar polarographic monitor has also been developed by Hersch [W. Bahmet and P. A. Hersch, Anal. Chem., 43, 803 (1971) and P. A. Hersch, Amer. Lab, Aug. 1973, p. 29] and is based on the linear variation of the limiting current attainable from a cadmium-air cell when the partial pressure of oxygen is varied. There are two very major problems with such electrochemical methods, they depend on the precise maintenance of solution concentration, and they depend upon a kinetically limited gas liquid equilibrium system. One can speculate optical methods since these methods could theoretically be based on any colorimetric oxygen reaction.

Mass spectrometry and gas chromatography, however, are the methods conventionally used for the quantitative and qualitative analysis of gases, and could easily be adapted to oxygen monitoring. A major consideration in their use, however, would be their relative cost and size. A detector based specifically on the paramagnetic properties of oxygen is also conceivable, but seems even less promising than mass spectrometry or gas chromatography on the basis of cost, size and versatility. Thus, simple optical systems are purely speculative, while instrumental procedures are too complex and too expensive.

Transistor devices have also been suggested. CHEMFET devices have been proposed for monitoring systems. Use of these chemically sensitive field effect transistor devices [J. Janata and R. H. Huber, in "Ion-Selective Electrodes", Analytical Chemistry, Vol. 2, H. Freiser, ed., Plenum Press, New York, 1980, pp. 124–6] is predicated on the measurement of changes in the source/drain current passing through a transistor due to variations in the electric field in the gate region of the device. The observed changes in current could, for example, result from the absorption of oxygen on, or its reaction with, material, in the gate region of the device.

Charge-flow transistors have also been suggested. Application of these devices [S. L. Garverick and S. D. Senturia, IEEE Trans. Electron Dev., 29, 90 (1982)] involves the measurement of the change in admittance (AC conductance) of a transistor resulting from the adsorption of a given species (e.g. $O_2$) on, or its reaction with, a resistive material placed in the gate region of the device. The admittance of the device is directly related to the time delay observed between the application of a gate-to-source voltage and the initiation of the source-to-drain current. Both CHEMFET devices and charge-flow transistors tend to be very complex systems overall, and yet are very unreliable.

None of the teachings heretofore available provide a truly inexpensive and completely reliable apparatus andor method by which the oxygen content of a gas or atmosphere can be continuously and reversibly monitored over an indefinite period of time using nondepletable materials and, insofar as the monitoring element, no moving parts. It will be appreciated that a serious need exists to monitor the oxygen content of a gas feed stream or the atmosphere within a container, chamber, room, or the like, to maintain continuous monitoring with instantaneous warning in the event of an undue pressure drop. Such systems and apparatus would have particular utility and applicability in medical applications, such as monitoring the oxygen feed to a patient and/or the oxygen content of the atmosphere within an oxygen tent or room. Such monitoring is now possible, if at all, only using extremely cumbersome and expensive equipment.

IN THE DRAWINGS

FIG. 1 is a schematic illustration of one embodiment of the present invention.

FIG. 2 is a schematic diagram of the circuitry of a device suitable for use in the practice of the present invention.

SUMMARY OF INVENTION

We have now discovered a novel method and apparatus which can provide continuous monitoring of the oxygen content of a gas over an indefinite period of time and at a minimal cost. The method and apparatus of our invention provides an instantaneous response to critical changes in oxygen level independent of the level of humidity, and without the need for the use of pH sensitive indicators, or expensive and sophisticated analytical instruments.

FIG. 1 is a schematic diagram of the apparatus of the present invention including defined area 1 having input port 2 by which gas is fed into said area, and egress means 3 by which gas may leave the area. Disposed within said area is a light source 4 and a light detection means 5 is shown coupled to a warning device 6, a manganese tertiary phosphine polymer complex 7 is deposited between said light source and said light detection means.

In the novel apparatus of the present invention, a light source and a light sensitive detector are disposed within the atmosphere to be measured, and a polymeric film formed from a manganese tertiary phosphine polymer complex is deposited between the light source and the detector. The detector in turn is suitably connected to an audio and/or visual warning device and/or a recorder which will provide the desired form of warning.

Applicants' co-pending, commonly assigned application Ser. No. 607,513 filed May 7, 1984, now U.S. Pat. No. 4,544,707 discloses and claims certain novel manganese tertiary phosphine polymer complexes.

The manganese tertiary phosphine polymer complexes are prepared by adding a manganese salt to an anhydrous solution of a polymer selected from the group consisting of polyvinylchloride, silicone, polyvinylacetate, and polystyrene, in a suitable solvent, then adding a monodentate ligand to the polymer-manganese salt solution. These polymer compositions will reversibly complex with gases such as oxygen. The manganese salt corresponds to the formula:

$$MnX_2$$

wherein X is a species capable of forming an anion; and the ligand is a compound of the formula:

$$PR^1R^2R^3$$

wherein $R^1$, $R^2$, and $R^3$ may be the same or different, and is selected from the group consisting of substituted or unsubstituted alkyl, cycloalkyl or aryl groups or hydrogen, provided that at least one of the groups $R^1$, $R^2$, and $R^3$ is a substituted or unsubstituted alkyl, cycloalkyl or aryl group.

While elevated temperatures may be required to dissolve the starting polymer in the solvent such as tetrahydrofuran the remainder of the synthesis can generally be carried out at room temperature, though preferably under anhydrous conditions. The polymer content of the starting polymer solution can vary widely and is primarily dependent on the amount of solvent needed to maintain suitable handling conditions such as any desired viscosity or the like. A 2% to 30% by weight solution is generally considered operable, and a 5% to 20% by weight solution is preferred.

The weight ratio of manganese salt to starting polymer is usually in the range of about 1:10 to 2:1 and preferably about 1:2 to 2:1. The ligand is added as at least a stoichiometric equivalent of the manganese salt, and preferably as a stoichiometric excess of 50% to 150%.

Ligands of particular interest include those within the following groups:

Phenyldialkylphosphines, diphenylalkylphosphines, cyclohexyldialkylphosphines, dicyclohexylalkylphosphines, trialkylphosphines, including methyldialkylphosphines, ethyldialkylphosphines, pentyldialkylphosphines, octyldialkylphosphines, and dodecyldialkylphosphines. The following specific ligands are generally regarded as of interest, trimethylphosphine, triethylphosphine, tributylphosphine, methyldiethylphosphine, ethylimethylphosphine, dimethylphenylphosphine, diethylphenylphosphine, methyldiphenylphosphine, diphenylethylphosphine, trioctylphosphine, in which the alkyl group is preferably a straight chain alkyl group.

A film can be cast from the solution of the polymer composition by any of a variety of widely known techniques well known to those skilled in the art. Once the film is cast, as it absorbs oxygen the intensity of the color of the film will change getting darker or more intense as more oxygen is absorbed—or lighter as the process is reversed and oxygen is released. The particular color evidenced by a given film produced from a polymer composition containing a given ligand will vary according to the specific X moiety employed.

By casting a film inside a tube used to conduct oxygen to a hospital patient, it is possible to monitor oxygen supply using a photosensitive metering device which can be triggered by a change in oxygen concentration of the gas being delivered to the patient. If the concentration of oxygen were to drop below a predetermined critical limit, there would be a change in the color intensity of the film, in this case becoming lighter, which would permit transmission of a sufficient intensity of light to reach the photosensitive metering device, thereby triggering suitable alarms.

PREFERRED EMBODIMENT

The preferred polymer compositions for use with the present invention are prepared with ligands of the formula:

$$PR^1R^2R^3$$

wherein $R^1$ and $R^2$ may be the same or different, and each is selected from the group consisting of alkyl and substituted alkyl moieties having 1 to 12, preferably 2 to 18 carbon atoms; and $R^3$ is selected from the group consisting of alkyl and substituted alkyl moieties having 1 to 12, preferably 2 to 18 carbon atoms and aromatic moieties having from 6 to 18 and preferably 6 to 10 carbon atoms.

EXAMPLE 1

O₂ Gas Sensor

A film was cast from a complex of tri-n-butylphosphine-THF-PVC-manganese (II) thiocyanate which was prepared as described in example 2 of co-pending application Ser. No. 607,513 filed May 7, 1984, now U.S. Pat. No. 4,544,707.

A freshly prepared 1"×1" film of the complex tri-n-butylphosphine-THF-PVC-manganese (II) thiocyanate was sandwiched between two 2"×3" Lexan plastic blocks. These blocks were bolted together to form the detection cell. Air flowed across the film in the cell via a ¼" diameter channel bisected by the two cell halves. In one block on one side of the film a green LED source (Radio Shack No. 276-022) was mounted. Opposite the source on the other side of the film in the adjacent block a CdS photocell detector (Radio Shack 276-116) was mounted. To eliminate stray light the entire cell was painted and further covered with black electrical masking tape.

For experimental evaluation, the level of $pO_2$ in argon was varied. Breathable levels of $pO_2$ give the film the deepest red color and a maximum electrical resistance across the photocell. As the $pO_2$ decreases, the film color lightens. More illumination from the LED is transmitted across the film to the photocell detector causing the electrical resistance across it to decrease. Depending on LED intensity, film thickness, and $pO_2$ the photocell resistance can vary from 100 ohm to 100 Kohm.

EXAMPLE 2

Oxygen Level Change Alarm

The oxygen gas sensor described in example 1 was integrated into an inexpensive alarm system that provides a warning that the $pO_2$ level has changed. A piezoelectric speaker (Radio Shack No. 273-064) provided an audible alarm while a yellow to red LED (Radio Shack No. 276-035) provides a visual alarm.

The photocell was incorporated into a programmable light meter circuit as illustrated by FIG. 2, [*Engineer's Notebook II, A Handbook of Integrated Circuit Applications*, by Forest M. Mins, III, *First Edition*, 1982, page 87] at PC1, R1 and R3 are external potentiometers with a variable resistance from 1 Kohm to 1 Mohm. In operation, for a given level of $pO_2$, LED source light intensity, and film thickness, the resistance across PC1 is constant. Both R1 and R3 are adjusted until the alarm signals cease. If the $pO_2$ level changes, the photocell resistance changes. Using the aforementioned circuit, the result is both an audible buzzing and a change in LED color from yellow to red. This signals the change in $pO_2$ level measured by the gas sensor.

In general the manganese thiocyanate-PVC-phosphine polymer compositions were found to provide the most "heme-like" films, and their moisture insensitivity seemed to increase with the chain lengths of trialkyl substituted phosphines. This is to say, polymer compositions, where the ligand was trioctyl phosphine, showed better moisture insensitivity than those in which the ligand was tributyl phosphine, which in turn showed better moisture insensitivity than compositions prepared using triethyl phosphine. In addition polymeric compositions, wherein the starting polymer was silicone showed better moisture insensitivity than polymer compositions prepared using PVC or polystyrene. Polymeric compositions, wherein the starting polymer was polystyrene, tended to exhibit greater color intensity at low oxygen concentrations, which might make them particularly useful in application wherein it is necessary to be alerted to even relatively low concentrations of oxygen.

While we are not willing to limit ourselves to any one theory by which the novel method, compositions, or properties of our invention might be explained, it would appear likely that some type of crosslinking or complexing is taking place between two or more of the manganese salt, the phosphine, the tetrahydrofuran and/or the starting polymer. It would also appear that the significantly improved rates of absorption and desorption of gas exhibited by the films prepared from the novel polymer compositions of the present invention may be attributable to a significantly increased exposed surface area of gas complexing agent, as compared to the exposed surface area of prior art materials such as those employed by McAuliffe et al., as coating on a particulate support.

Alternatively, the ligand, polymer, manganese halide, and solvent complex may alter the activation barrier or energetics for gas absorption and desorption by the heme analogue.

The compositions of the present invention may be used in any form, shape, or configuration in which the starting polymer is conventionally employed, using any conventional casting technique. It has been noted that one of the most obvious use of the novel polymer compositions of the present invention, would be in the form of a film. It will be understood by those skilled in the art, that the specific conditions under which the film is to be cast, the techniques employed in laying down the film, and the environmental and other conditions under which the film will be employed, may require the use of other and additional materials such as heat, or light stabilizers, wetting agents and other similar additives well known to those skilled in the art. Suitable additives may be combined with the novel compositions of the present invention without substantially altering the advantages set forth hereinbefore.

It will be course also be obvious that other changes, modifications and alterations can be made in the compositions and methods herein described without departing from the scope of the invention herein disclosed and it is our intention to be limited only by the appended claims.

As our invention we claim:

1. Apparatus for monitoring the oxygen content in a stream of gas comprising a housing means; a light source, and a light detection means disposed within said housing means, and in alignment with each other, said detection means being coupled to a warning device; a film of manganese tertiary phosphine polymer complex disposed between said light source and said light detection means; input means by which the gas to be monitored is fed into said housing; and egress means from said housing.

2. The apparatus according to claim 1 wherein the polymer in the complex is silicone.

3. The apparatus according to claim 1 wherein said light source is a LED light source.

4. The apparatus according to claim 1 wherein said polymer complex is produced by the steps which comprise: forming a substantially anhydrous first solution of a polymer selected from the group consisting of polyvinylchloride, polystyrene, polyvinylacetate, and silicone, dissolved in a suitable solvent; adding a substantially anhydrous manganese salt of the formula:

$$MnX_2$$

wherein X is a species capable of forming an anion to form a second solution, then adding to the solution of polymer and manganese salt at least a stoichiometric equivalent with respect to said manganese salt of a substantially anhydrous phosphine of the formula:

$$PR^1R^2R^3$$

wherein $R^1$, $R^2$, and $R^3$ may be the same or different, and each is selected from the group consisting of substituted or unsubstituted alkyl, cycloalkyl or aryl groups or hydrogen, provided that no more than two of the groups $R^1$, $R^2$, and $R^3$ are substituted or unsubstituted aryl groups and that at least one of the groups $R^1$, $R^2$, and $R^3$ is a substituted or unsubstituted alkyl, cycloalkyl or aryl group.

5. The apparatus according to claim 4 wherein X is a member selected from the group consisting of chlorine, bromine, iodine and thiocyanate, and said solvent is tetrahydrofuran.

6. The apparatus according to claim 4 wherein a stoichiometric excess of phosphine is employed.

7. The apparatus of claim 4 wherein said phosphine is selected from the group consisting of methyldialkylphosphines, ethyldialkylphosphines, and pentyldialkylphosphines.

8. The apparatus of claim 4 wherein said polymer comprises between about 2 and 30 wt.%, inclusive, of said first solution, the weight ratio of said manganese salt to said polymer is in the range of about 1:10 to 2:1, inclusive, and said phosphine is added in a stoichiometric excess with respect to said manganese salt of between about 50 and 150%, inclusive.

9. The apparatus of claim 8 wherein said polymer comprises between about 5 and 20 wt.%, inclusive, of said first solution and said weight ratio of said manganese salt to said polymer is between about 1:2 and 2:1, inclusive.

10. The apparatus according to claim 4 wherein said phosphine is selected from the group consisting of phenyldialkylphosphines, diphenylalkylphosphines, cyclohexyldialkylphosphines, dicyclohexylalkylphosphines, trialkylphosphines, octyldialkylphosphines, and dodecyldialkylphosphines.

11. The apparatus according to claim 10 wherein said phosphine is selected from the group consisting of trimethylphosphine, triethylphosphine, tributylphosphine, methyldiethylphosphine, ethyldimethylphosphine, dimethylphenylphosphine, diethylphenylphosphine, methyldiphenylphosphine, diphenylethylphosphine, and trioctylphosphine.

12. The apparatus according to claim 10 wherein said polymer is polyvinylchloride.

13. A method of monitoring the oxygen content of a stream of gas the steps which comprise passing the gas to be monitored through a defined enclosed area, disposing a light source and light detection means within said enclosed area and in alignment with each other, disposing a film of manganese tertiary phosphine polymer complex between said light source and said detection means, connecting said detection means to a warning device whereby a drop in the oxygen content in the gas stream will cause a reduction in the color intensity of the said film permitting light to pass through the film activating the light detection means and thereby activating said warning device.

14. The method according to claim 13 where said polymer complex is synthesized by the steps which comprise: forming a substantially anhydrous first solution of a polymer selected from the group consisting of polyvinylchloride, polystyrene, polyvinylacetate, and silicone, dissolved in a suitable solvent; adding a substantially anhydrous manganese salt of the formula:

$$MnX_2$$

wherein X is a species capable of forming an anion to form a second solution; then adding to the solution of polymer and manganese salt at least a stoichiometric equivalent with respect to said manganese salt of a substantially anhydrous phosphine of the formula:

$$PR^1R^2R^3$$

wherein $R^1$, $R^2$, and $R^3$ may be the same or different, and each is selected from the group consisting of substituted or unsubstituted alkyl, cycloalkyl or aryl groups or hydrogen, provided that no more than two of the groups $R^1$, $R^2$, and $R^3$ are substituted or unsubstituted aryl groups and that at least one of the groups $R^1$, $R^2$, and $R^3$ is a substituted or unsubstituted alkyl, cycloalkyl or aryl group.

15. The method according to claim 14 wherein a stoichiometric excess of phosphine is employed.

16. The method according to claim 14 wherein the polymer in the complex is silicone.

17. The method according to claim 14 wherein said light source is a LED light source.

18. The method of claim 14 wherein said phosphine is selected from the group consisting of methyldialkylphosphines, ethyldialkylphosphines, and pentyldialkylphosphines.

19. The method according to claim 14 wherein said solvent is tetrahydrofuran.

20. The method according to claim 19 wherein X is a member selected from the group consisting of chlorine, bromine, iodine and thiocyanate.

21. The method of claim 14 wherein said polymer comprises between about 2 and 30 wt.%, inclusive, of said first solution, the weight ratio of said manganese salt to said polymer is in the range of about 1:10 to 2:1, inclusive, and said phosphine is added in a stoichiometric excess with respect to said manganese salt of between about 50 and 150%, inclusive.

22. The method of claim 21 wherein said polymer comprises between about 5 and 20 wt.%, inclusive, of said first solution and said weight ratio of said manganese salt to said polymer is between about 1:2 and 2:1, inclusive.

23. The method according to claim 14 wherein said phosphine is selected from the group consisting of phenyldialkylphosphines, diphenylalkylphosphines, cyclohexyldialkylphosphines, dicyclohexylalkylphosphines, trialkylphosphines, octyldialkylphosphines and dodecyldialkylphosphines.

24. The method according to claim 23 wherein said phosphine is selected from the group consisting of trimethylphosphine, triethylphosphine, tributylphosphine, methyldiethylphosphine, ethyldimethylphosphine, dimethylphenylphosphine, diethylphenylphosphine, methyldiphenylphosphine, diphenylethylphosphine, and trioctylphosphine.

25. The method according to claim 23 wherein said polymer is polyvinylchloride.

* * * * *